United States Patent
Takada et al.

(10) Patent No.: US 7,057,169 B2
(45) Date of Patent: *Jun. 6, 2006

(54) PROBING METHOD USING ION TRAP MASS SPECTROMETER AND PROBING DEVICE

(75) Inventors: Yasuaki Takada, Kiyose (JP); Minoru Sakairi, Tokorozawa (JP)

(73) Assignee: Hitachi, Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 11/123,202

(22) Filed: May 6, 2005

(65) Prior Publication Data

US 2005/0199801 A1 Sep. 15, 2005

Related U.S. Application Data

(63) Continuation of application No. 10/311,270, filed as application No. PCT/JP00/06411 on Sep. 20, 2000, now Pat. No. 6,894,276.

(51) Int. Cl.
*H01J 49/42* (2006.01)
(52) U.S. Cl. .................................. 250/292; 250/282
(58) Field of Classification Search .............. None
See application file for complete search history.

(56) References Cited

U.S. PATENT DOCUMENTS

| | | | |
|---|---|---|---|
| 4,931,639 A | 6/1990 | McLafferty | |
| 5,206,509 A | 4/1993 | McLuckey et al. | |
| 5,481,107 A | 1/1996 | Takada | |
| 5,612,534 A | 3/1997 | Mimura | |
| 6,147,348 A | 11/2000 | Quarmby | |
| 6,295,860 B1 | 10/2001 | Sakairi | |
| 6,894,276 B1 * | 5/2005 | Takada et al. | 250/292 |

FOREIGN PATENT DOCUMENTS

| | | |
|---|---|---|
| JP | 7-85834 | 3/1995 |
| JP | 7-502142 | 3/1995 |
| JP | 7-134970 | 5/1995 |
| JP | 11-230918 | 8/1999 |
| JP | 2000-28579 | 1/2000 |

* cited by examiner

*Primary Examiner*—Jack I. Berman
(74) *Attorney, Agent, or Firm*—Antonelli, Terry, Stout and Kraus, LLP.

(57) ABSTRACT

An analyzing method using a tandem mass spectrometric apparatus includes a first analysis step of acquiring a mass spectrum, a decision step of deciding if ions of a predetermined m/z value are present, and a second analysis step of acquiring a tandem mass spectrum according to the decision results from the first analysis step.

9 Claims, 12 Drawing Sheets

(a) AMPLITUDE OF AN RF SIGNAL APPLIED TO THE RING ELECTRODE
(b) AMPLITUDE OF AN RF SIGNAL APPLIED TO THE ENDCAP ELECTRODES

FIG. 6

(a) AMPLITUDE OF AN RF SIGNAL APPLIED TO THE RING ELECTRODE
(b) AMPLITUDE OF AN RF SIGNAL APPLIED TO THE ENDCAP ELECTRODES

(a) AMPLITUDE OF AN RF SIGNAL APPLIED TO THE RING ELECTRODE
(b) AMPLITUDE OF AN RF SIGNAL APPLIED TO THE ENDCAP ELECTRODES

(a) AMPLITUDE OF AN RF SIGNAL APPLIED TO THE RING ELECTRODE
(b) AMPLITUDE OF AN RF SIGNAL APPLIED TO THE ENDCAP ELECTRODES

PROBING METHOD USING ION TRAP MASS SPECTROMETER AND PROBING DEVICE

CROSS REFERENCE TO RELATED APPLICATION

This application is a continuation of U.S. application Ser. No. 10/311,270, filed Dec. 13, 2002, now U.S. Pat. No. 6,894,276, which is a 371 of PCT/JP00/06411, filed Sep. 20, 2000, the contents of which are incorporated by reference herein.

TECHNICAL FIELD

The present invention relates to techniques for detecting explosives and drugs, and particularly to a detecting device using ion trap mass spectrometer.

BACKGROUND ART

Detecting devices are demanded for detecting explosives in order to prevent terrorism and maintain security in the midst of the aggravated international conflicts. Baggage inspection apparatus using X-ray transmission are now widely used as detecting devices chiefly in airports. Since the X-ray detecting device detects objects as lumps and identifies dangerous materials from information of shape, it is called bulk detection. The detecting method based on gas analysis is called trace detection, and used to identify substances from chemical analysis information. The trace detection is characterized in that very small amounts of ingredients attached to a baggage or the like can be detected. A security scanner of greater precision is desired to produce by combining bulk detection and trace detection in order to socially strengthen the security.

Custom offices also use detecting devices in order to detect forbidden chemicals sneaked through various routes. Although bulk detectors and drug-sniffing dogs are chiefly used in custom offices, a trace analyzer for forbidden chemicals is eagerly desired to produce in place of the drug-sniffing dogs.

Various analyzing methods such as ion mobility spectroscopy and gas chromatography have been tried as trace detection. Research is being conducted for developing apparatus having high speed, high sensitivity and high selectivity as important factors in the detecting device.

In these situations, a detecting method based on mass spectrometry is proposed that is fundamentally excellent in speed, sensitivity and selectivity as, for example, disclosed in JP-A-7-134970. A conventional detecting device based on mass spectrometry will be described with reference to FIG. 16.

Figure 16:
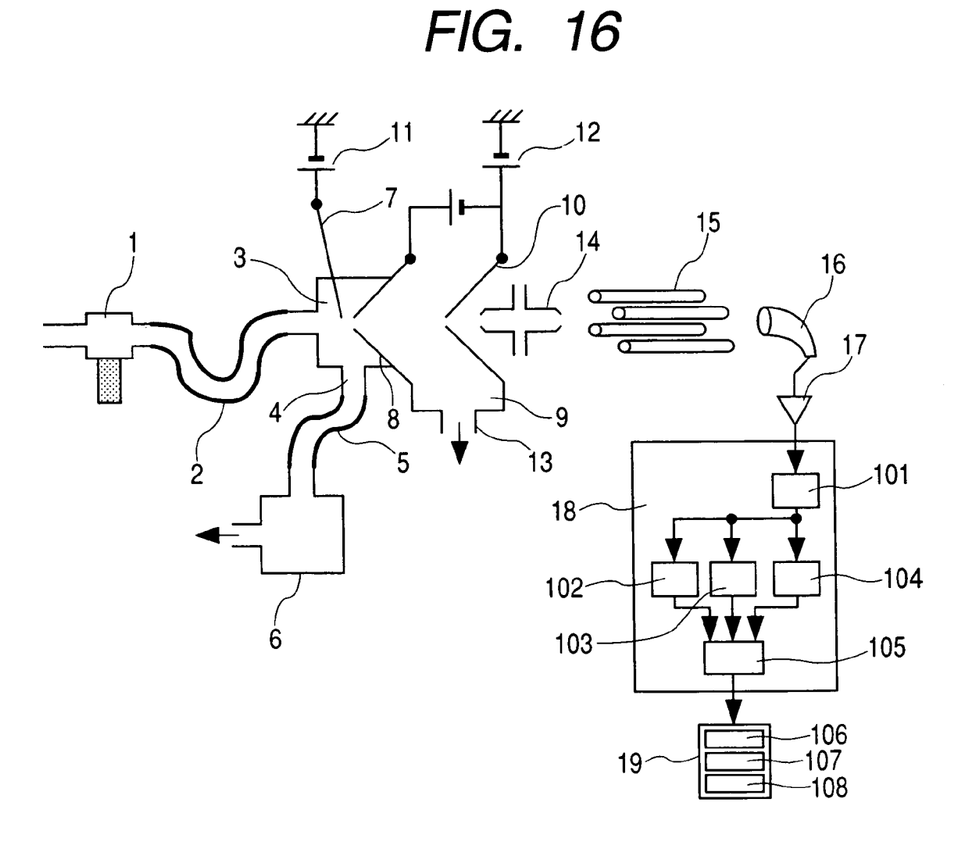
FIG. 16 is a diagram showing the construction of the conventional mass spectrometer used for detecting dangerous objects.

An air suction probe 1 is connected through an insulation pipe 2 to an ion source 3. The ion source 3 is connected through an exhaust port 4 and an insulation pipe 5 to an air exhaust pump 6. The ion source 3 has a needle electrode 7, a first aperture electrode 8, an intermediate pressure portion 9 and a second aperture electrode 10. The needle electrode 7 is connected to a power source 11, and the first aperture electrode 8 and second aperture electrode 10 are connected to an ion accelerating power source 12. The intermediate pressure portion 9 is connected through an exhaust port 13 to a vacuum pump. An electrostatic lens 14 is disposed in the stage succeeding the intermediate pressure portion. A mass spectrometric portion 15 and a detector 16 are disposed in the stage succeeding the electrostatic lens 14. A detected signal from the detector 16 is supplied through an amplifier 17 to a data processor 18. The data processor 18 detects a plurality of m/z values (mass number of ion/valence of ion) of particular chemicals, thus deciding if the detected gas contains a particular chemical.

This data processor 18 has a mass determining section 101, a drug-A determining section 102, a drug-B determining section 103, a drug-C determining section 104 and an alarm driving section 105. An alarm display 19 that is driven by the alarm driving section 105 has display portions 106, 107, 108 disposed.

DISCLOSURE OF THE INVENTION

The above prior art has the following drawbacks.

The above device detects chemicals by using the m/z values of ions generated by the ion source. Therefore, when a chemical substance exists that generates ions of the same m/z values as those of the detected drug, there is a possibility that an alarm is issued despite the fact that there is no drug.

More specifically, there is the problem that while the device is detecting an awakening drug within baggage, it may misreport in response to the ingredients of a beauty product stored in the baggage. This misreport is caused by low selectivity of the mass spectrometric portion for analyzing ions, or when the device cannot distinguish the ions of the drug incidentally having the same m/z values from the ions of cosmetics.

Tandem mass spectrometry is known as a method of increasing the selectivity in the mass spectrometer. As devices for implementing the tandem mass spectrometry, there are triple quadrupole mass spectrometer and quadrupole ion trap mass spectrometer. In the tandem mass spectrometry, the following steps are performed:

(1) First-stage mass analysis, in which mass analysis is made to measure the m/z values of ions generated by the ion source;

(2) Selection, in which ions having a particular m/z value are selected from the ions having various m/z values;

(3) Dissociation, in which the selected ions (precursor ions) are dissociated by collision with neutral gas to produce resolvent ions (fragment ions); and (4) Second-stage mass analysis, in which mass analysis is made for fragment ions.

When the precursor ions are dissociated, the strength of chemical bond at each place of the molecule determines where the molecule is cut away. Therefore, analyzing the fragment ions will make it possible to obtain a mass spectrum containing an extreme abundance of molecular structure information of precursor ions. Accordingly, even if the m/z values of ions generated by the ion source are the same by chance, it can be decided if the objects being detected are contained in pieces of baggage by examining the mass spectrum of fragment ions.

Thus, if the mass spectrometric portion 15 in the conventional probing device of FIG. 16 is replaced by a triple quadrupole mass spectrometer or quadrupole ion trap mass spectrometer to implement the tandem mass spectrometry, the selectivity can be improved, and the misreport can be reduced. However, the tandem mass spectrometry takes a longer time than the normal mass spectrometry, and thus the detecting speed of the detecting device cannot be improved.

For the above reasons, the detecting device has been requested to have high selectivity and high speed.

Accordingly, it is an object of the invention to provide a high-speed, less misreport detecting device for explosives and banned drugs by using fast screening mode and high-selectivity detailed checking mode.

BEST MODE FOR CARRING OUT THE INVENTION

Embodiments of the invention will be described in detail with reference to the accompanying drawings.

Figure 1:
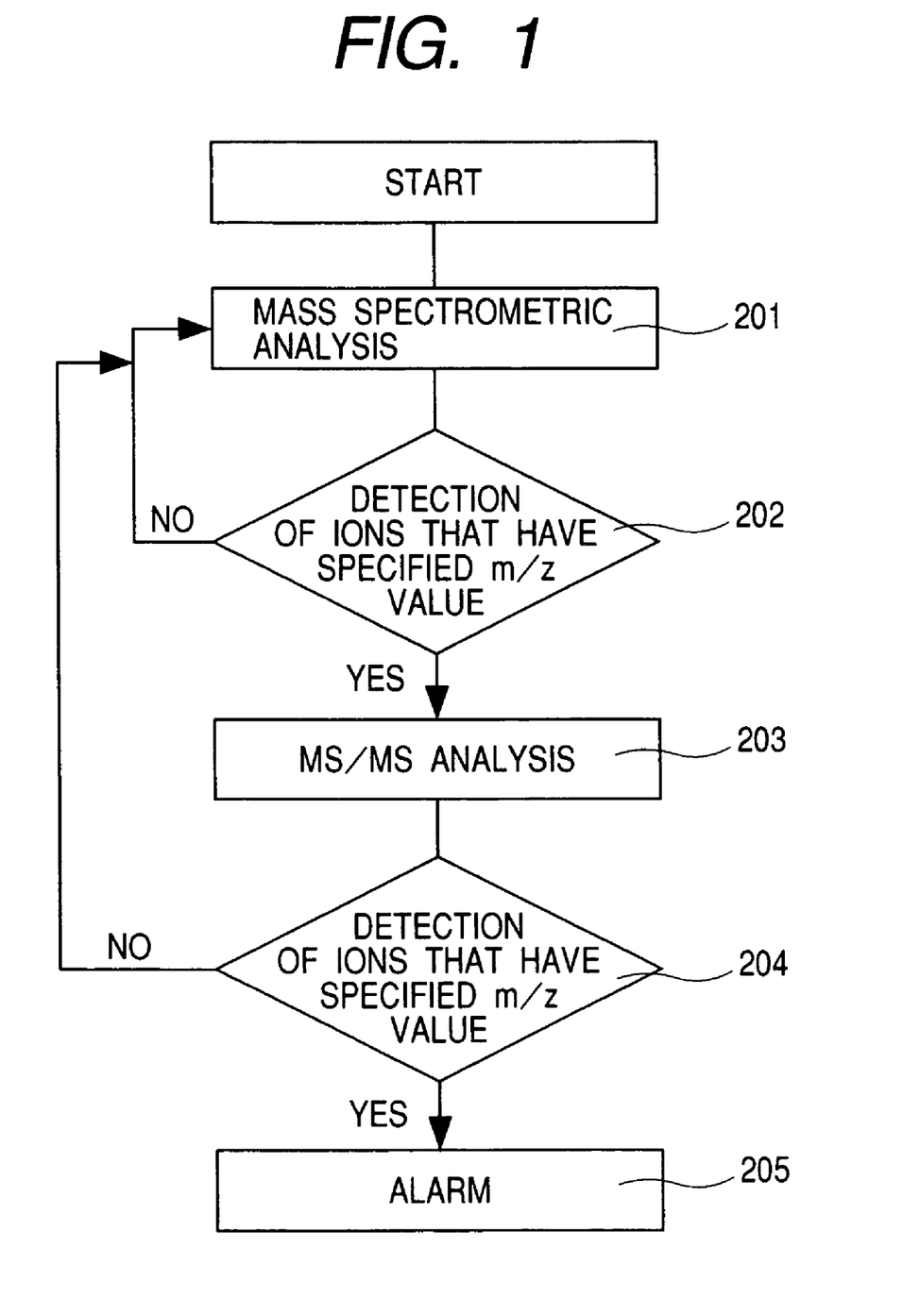
FIG. 1 is a diagram showing the algorithm of one embodiment of the invention.

FIG. 1 is a diagram showing the algorithm of the first embodiment of the invention.

The detecting method of this embodiment has a first analysis step 201 for acquiring mass spectrum, a first decision step 202 for deciding if there are ions of a first peculiar m/z value, a second analysis step 203 for tandem mass spectrometry according to the decision results in the first decision step 202, a second decision step 204 for deciding if there are ions of a second peculiar m/z value, and an announcement step 205 for issuing an alarm in accordance with the decision results in the second decision step 204. The measuring operation by the steps 201 and 202 is called as the screening mode, and the measuring operation by the steps 203 and 204 as the detailed checking mode.

To detect, in step 201 the ions generated from the sample gas are analyzed, and in step 202 it is decided if ions of the m/z value corresponding to that derived from the detected object are detected. For example, when amphetamine as a kind of stimulant drug is ionized in the positive atmospheric pressure chemical ionization mode, it produces pseudo molecular ions $(M+H)^+$ (M is sample molecule, and H is proton) that is the addition of proton to amphetamine molecule. Since the m/z value of the false molecular ions is 136, decision is made of if ions of 136 in m/z are detected in step 202 (first decision).

Here, the m/z value to be decided in step 202 is of course dependent upon the object to be detected. A plurality of different m/z values may be decided for various different narcotic drugs and stimulant drugs.

When the analysis time in the first analysis step 201 is selected to be 0.1 second, the results from the repetition of step 201 and integration of the measured results may be used for the decision in step 202. Since the random noise can be averaged by the integration, the error in step 202 can be reduced.

When ions of a predetermined first peculiar m/z value are decided to exist in step 202, the second analysis step 203 for tandem mass spectrometry (hereafter, MS/MS) is performed. Step 203 includes the processes of precursor-ion selection, precursor-ion dissociation, and mass spectrometry of fragment ions. In order to increase the analysis precision, longer time should be taken in step 203 than in step 201.

Step 203 can produce a mass spectrum with abundant molecular structure information. This mass spectrum is decided (second decision) in step 204 to have a m/z value peculiar to the object being detected or not. If it is present, the alarm is activated to send an alarm signal.

In step 204, if the mass spectrum of the object being detected by tandem mass spectrometry is previously measured and stored as database, referring to the database can make high precision decision.

The detecting method using the algorithm shown in FIG. 1 will be described below in more detail. During the detecting operation, the screening mode (namely, measurement in step 201 and decision in step 202) is repeated. If the decision in step 202 is made after the accumulation of 10 measurements each of which is selected to take 0.1 second for step 201, the total time necessary for the detecting becomes about 1 second. If the object being detected is doubted, or decided to be present in the baggage in step 202, the program goes to the high-selectivity detailed checking mode. If the decision in step 204 is also made after the accumulation of 10 measurements each of which is selected to take 0.5 second for step 203, the total detecting time including the screening mode beginning with step 201 becomes about six seconds. The baggage inspection associated with security gate should usually be completed in a few seconds including the times of the carrying in and setting of the baggage in the detecting device, detecting it and the carrying out of it. Therefore, the possible detecting time to be actually taken is in the range from one to two seconds. However, since the object to be detected is supposed not to be placed in most pieces of baggage, the detecting can be completed in about one second by the screening mode. Accordingly, use of the algorithm shown in FIG. 1 makes it possible to suppress the average detecting time to about 1~2 seconds per piece of baggage even if the device takes the time necessary for the processes up to the high-selectivity detailed checking mode. Thus, the baggage inspection can be made without remarkably interfering with the flow of baggage at the security gate. In addition, since the decision based on tandem mass spectrometry is finally performed by the high-selectivity detailed checking mode, the selectivity can be increased, and misreport can be reduced.

Since the detailed checking by tandem mass spectrometry takes much time as described above, an alarm lamp should be turned on or a signal for the operator to easily detect should be produced in the stage where the program goes to step 203 after the decision of step 202, or when the program shifts from the screening mode to the detailed checking mode.

Figure 2:
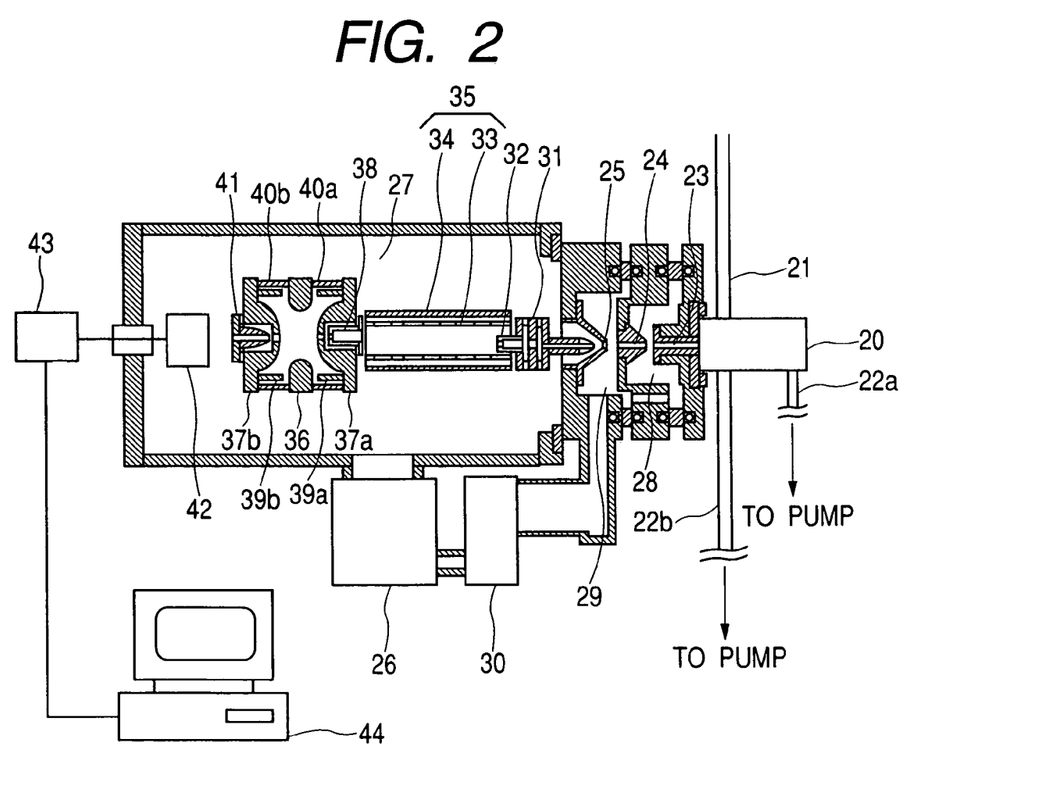
FIG. 2 is a diagram showing one example of the construction of a detecting device for embodying the invention.

FIG. 2 is a diagram showing the construction of the detecting device for embodying the invention. Here, a quadrupole ion trap mass spectrometer (thereafter, referred to as the ion trap mass spectrometer) is used for the mass spectrometry portion. An ion source 20 is coupled to a gas introduction tube 21, and exhaust pipes 22a, 22b. The gas from the gas sampling port is sucked in by a pump connected to the exhaust pipes 22a, 22b, and introduced through the gas introduction tube 21 to the ion source 20. The ingredients contained in the gas introduced into the ion source are partially ionized. The ions generated by the ion source and part of the gas introduced into the ion source are fed through first, second and third apertures 25, and taken in a vacuum space 27 that is evacuated by a vacuum pump 26. These apertures have a diameter of about 0.3 mm. The, electrodes of these apertures are heated up to a range from about 100° C. to 300° C. by a heater (not shown). The remaining gas not fed into the first aperture 23 is exhausted to the outside of the device from the exhaust pipes 22a, 22b through the pump.

There are differential evacuation spaces 28, 29 between the aperture electrodes 23, 24, 25, and these spaces are evacuated by a roughing pump 30. The roughing pump 30 is usually a rotary pump, scroll pump or mechanical booster pump. A turbo-molecular pump may be used for the evacuation of these regions. The aperture electrodes 23, 24, 25 to which voltages are applied thus improve the ion transmittance and split cluster ions generated due to adiabatic expansion by the collision with the residual molecules.

In the device shown in FIG. 2, a scroll pump of 900 liters per min is used for the roughing pump 30, and a turbo-molecular pump of 300 liters/min for the vacuum pump 26 that evacuates the vacuum space 27. The roughing pump 30 is also used dually as a pump for evacuating the back pressure side of the turbo-molecular pump. The pressure between the second and third apertures 24, 25 is about 1 torr. In addition, only the first and third apertures 23, 25 with the second aperture electrode 24 removed may be used to produce the differential evacuation space. However, since the gas inflow increases as compared with the previous case, it is necessary to increase the evacuation speed of the vacuum pump used and the distance between the apertures. Also in this case, it is important to apply a voltage between the apertures.

The generated ions are converged by a converging lens 31 after passing through the third aperture 25. This converging lens 31 is usually an Einzel lens formed of three sheets of electrode. The ions further pass through a slit electrode 32. The ions passed through the third aperture 25 are converged on the opening of the slit electrode 32 by the converging lens 31. The neutral particles that are passed but not converged collide with this slit portion, and thus they are not easy to arrive at the mass spectrometry portion side. The ions passed through the slit electrode 32 are deflected and converged by a double cylinder type deflector 35 that is formed of inner and outer cylinder electrodes 33, 34 having a large number of apertures. The double cylinder type deflector 35 deflects and converges the ions by using the electric field of the outer cylinder electrode that is leaked from the apertures of the inner electrode. The details are already disclosed in JP-A-7-85834.

The ions passed through the double cylinder type deflector 35 are introduced into the ion trap mass spectrometer that is formed of a ring electrode 36 and end cap electrodes 37a, 37b. A gate electrode 38 is provided to control the timing of the ions incident to the spectrometer. Flange electrodes 39a, 39b are provided to prevent the ions from arriving at quartz rings 40a, 40b that hold the ring electrode 36 and end cap electrodes 37a, 37b, charging the quartz rings 40a, 40b.

The inside of the ion trap mass spectrometer is filled with helium from a helium gas supply tube (not shown) so that it is maintained at a pressure of about $10^{-3}$ torr. A mass spectrometer controller (not shown) controls the ion trap mass spectrometer. The ions introduced into the mass spectrometer collide with helium gas to lose their energy, and are caught by an AC electric field. The caught ions are ejected out of the ion trap mass spectrometer in accordance with the m/z value of ions by scanning with the high-frequency voltage applied to the ring electrode 36 and end gap electrodes 37a, 37b, and the ejected ions are detected by a detector 42 through an ion ejecting lens 41. The detected signal is amplified by an amplifier 43, and then processed by a data processor 44.

Since the ion trap mass spectrometer has an ion trapping characteristic within the inside (the space surrounded by the ring electrode 36 and end cap electrodes 37a, 37b), the ions can be detected by increasing the ion introduction time even if the amount of ions is small due to low concentration of the substance being detected. Therefore, even if the sample concentration is low, the ion trap mass spectrometer can increase the concentration of the ions at a large magnifying power, and thus pretreatment (condensation) of sample can be very simplified.

Figure 3:
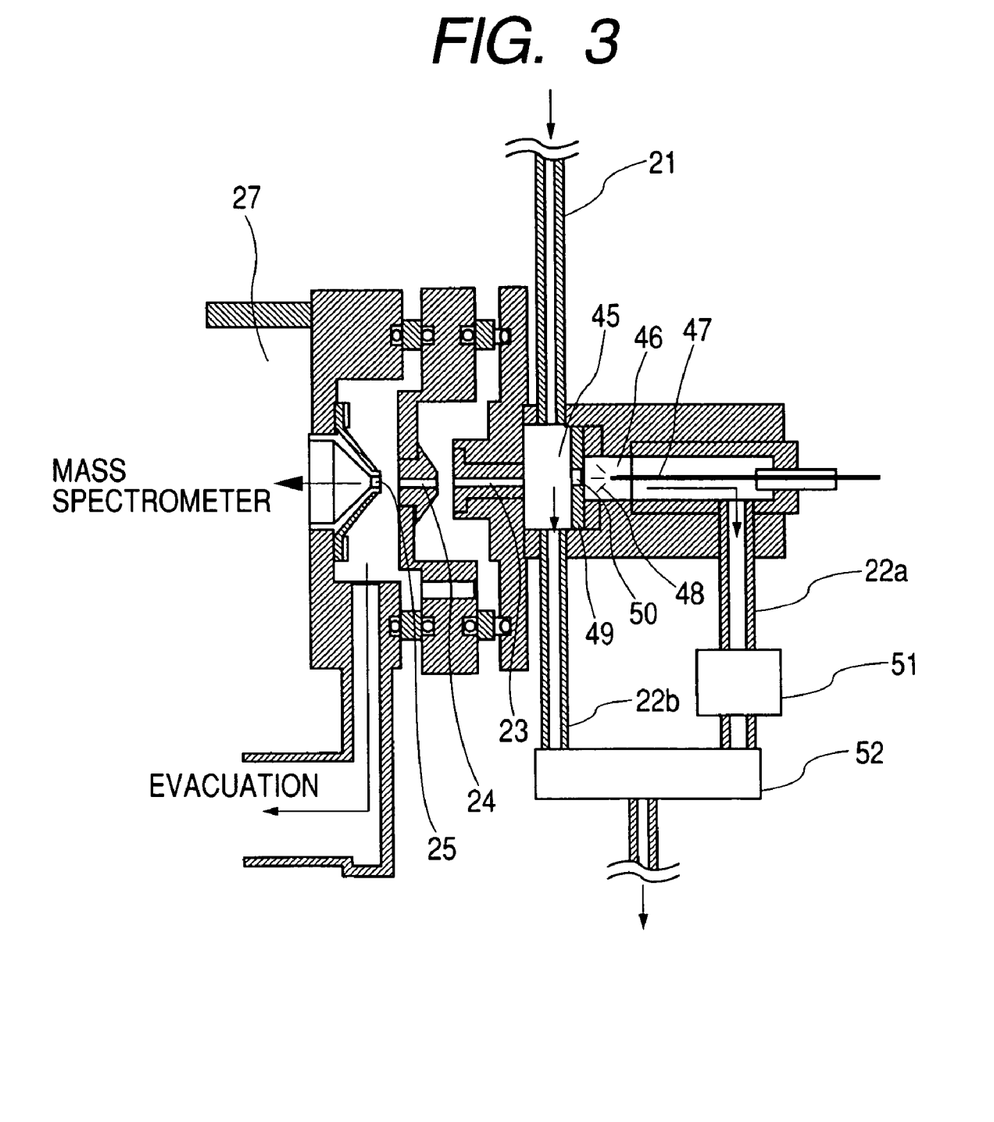
FIG. 3 is a diagram showing one example of the construction of the ion source for embodying the invention.

FIG. 3 is a magnified view of the ion source portion of the device shown in FIG. 2. The gas introduced through the sample gas introduction tube 21 is once introduced into an ion drift region 45. This ion drift region 45 is substantially kept at atmospheric pressure. Part of the sample gas introduced into the ion drift region is fed to a corona discharge space 46, and the remaining portion is exhausted out of the ion source through the exhaust pipe 22b. The sample gas introduced into the corona discharge space 46 is ionized when it is brought in a corona discharge region 48 generated at around the tip of a needle electrode 47 by applying a high voltage to the needle electrode 47. At this time, in the corona discharge region 48, the sample gas is introduced in the direction substantially opposite to the flow of ions that drift from the needle electrode 47 to the opposite electrode 49. The generated ions are introduced into the ion drift region 45 through an opening 50 of the opposite electrode 49 by an electric field. At this time, a voltage is applied between the opposite electrode 49 and the first aperture electrode 23, thereby drifting the ions so that the ions can be efficiently led to the first aperture 23. The ions introduced into the first aperture 23 are fed into the vacuum space 27 through the second and third apertures 24, 25.

The amount of gas flowing in the corona discharge space 46 is important for high-sensitive and stable detecting. Therefore, a flow controller 51 should be provided in the exhaust pipe 22a. In addition, a heater (not shown) should be used to heat the drift region 45, corona discharge space 46 and gas introduction tube 21 from the standpoint of sample suction prevention. Although the amount of gas flowing in the gas introduction tube 21 and exhaust pipe 22b can be determined by the throughput of a suction pump 52 such as a diaphragm pump and the conductance of the pipe arrangement, such a controller as the flow controller 51 shown in FIG. 3 may be provided in the gas introduction tube 21 or exhaust pipe 22b. By providing the suction pump 52 downstream relative to the ion generating area (namely, the corona discharge space 46) as viewed from the gas flow, it is possible to reduce the effect of the contamination (suction of sample) within the inside of the suction pump 52.

Figure 4:
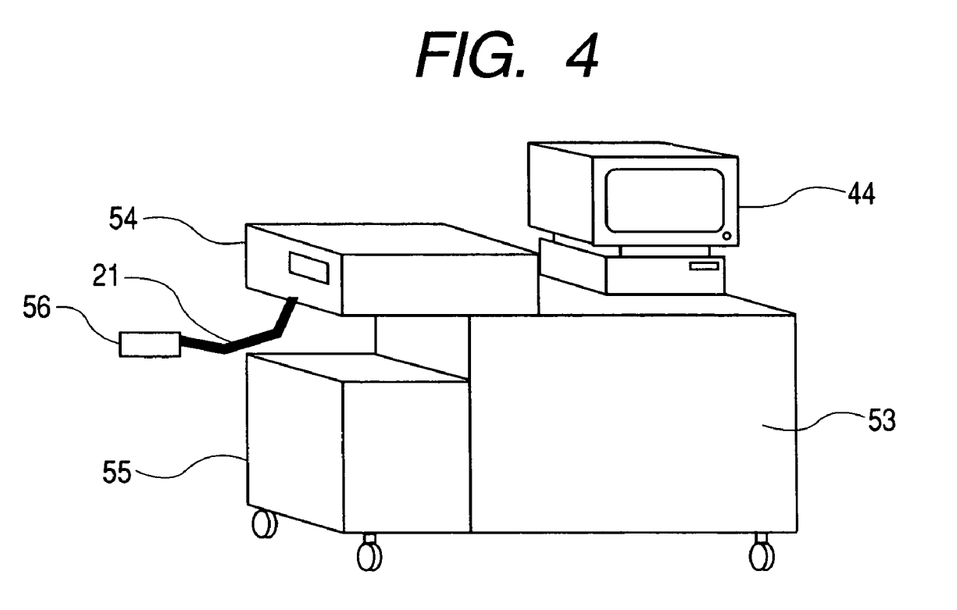
FIG. 4 is a diagram showing the construction of the vapor-sampling portion for embodying the invention.

FIG. 4 is a diagram showing one example of the sample-gas collecting portion of the device according to the invention. The detecting device is roughly divided into a main body 53, a gas suction unit 54, a case 55, and the data processor 44. The gas suction unit 54 is connected through the gas introduction tube 21 to a probe 56. The operator handles the probe 56 to bring it near a baggage or the like so that the air around the baggage can be sucked and detected.

Figure 5:
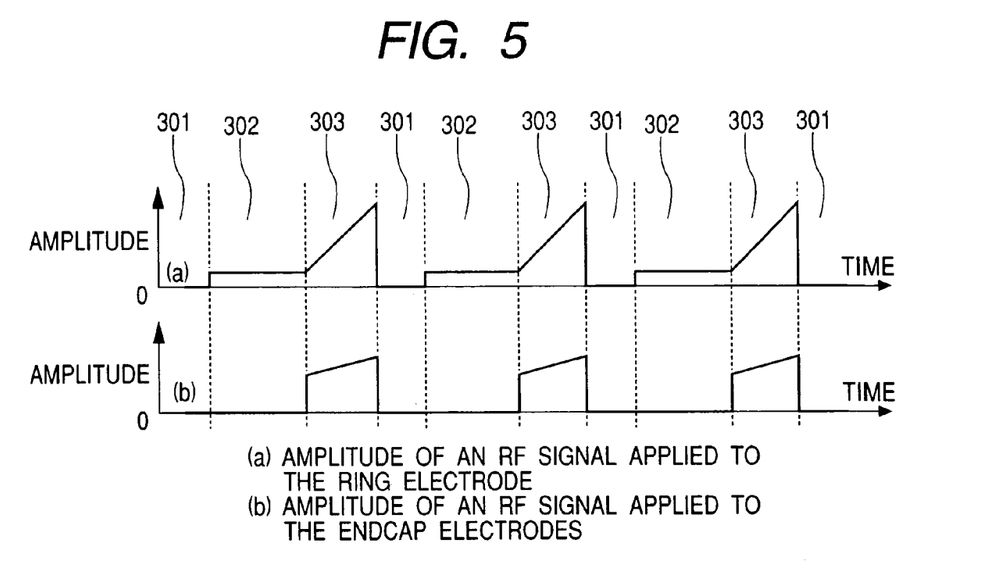
FIG. 5 is a timing chart of the voltage application in the embodiment of the invention.
Figure 6:
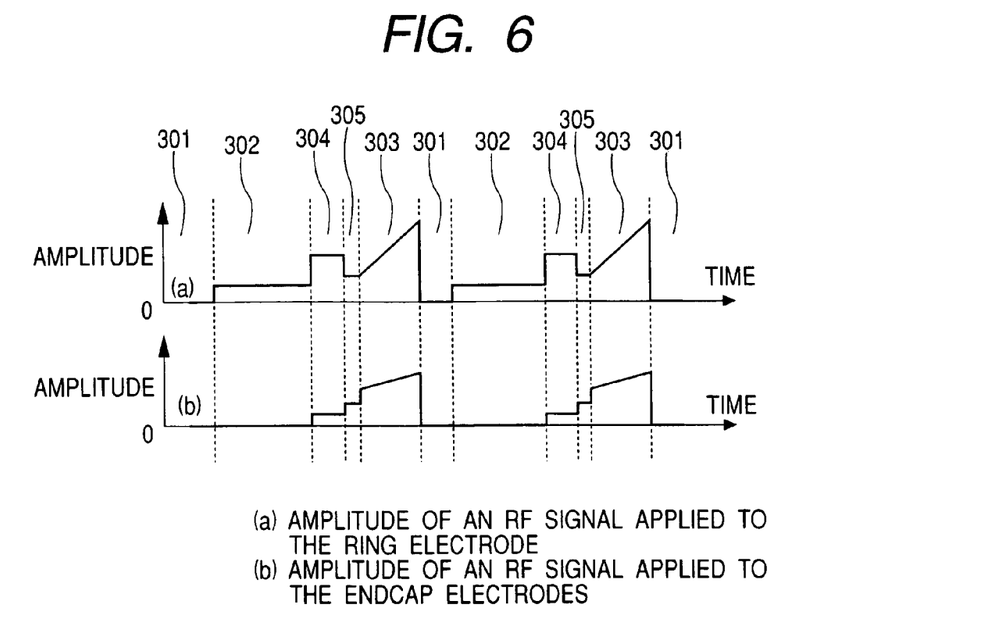
FIG. 6 is a diagram showing the procedure of MS/MS spectrometry in the embodiment of the invention.

The operation of the ion trap mass spectrometer in the embodiment of the invention will be described just for reference. FIG. 5 and FIG. 6 are timing charts of the voltages applied to the ring electrode and end cap electrodes. FIG. 5 shows the operation in step 201 of FIG. 1, and FIG. 6 shows the operation in step 203.

In step 201, in the ion trapping time interval, 302, a high frequency voltage is applied to the ring electrodes to generate an electric field for catching ions within the mass spectrometer. In addition, the voltage applied to the gate electrode is adjusted to control the ions to be introduced through the gate electrode into the mass spectrometer. Then, in the analyzing time interval, 303, the voltage applied to the gate electrode is adjusted to prevent the ions from further flowing in. The amplitudes of the high-frequency voltages applied to the ring electrode and end cap electrodes are controlled so that ions of different m/z values can be sequentially ejected out of the spectrometer within which the ions exist caught by the electric field. The detector then detects the ejected ions to produce a mass spectrum. In the residual ion removing time interval, 301, the ions remaining within the mass spectrometer are removed by turning off the voltage applied to the ring electrode.

The ion trapping time interval 302, analyzing time interval 303 and residual ion removing time interval 301 are selected to be typically 0.04 second, 0.05 second and 0.01 second, respectively. Thus, the mass spectrum can be produced once in 0.1 second. If the sample air concentration is so rare to need high sensitivity, the ion trapping time interval 302 may be extended.

The operation in step 202 will be described with reference to FIG. 6. The operations in the ion trapping time interval 302 and analyzing time interval 303 are the same as in step 201. In the selection time interval, 304, ions of predetermined m/z values are selected from the various ions trapped in the ion trapping time interval 302, and caused to remain, and the other ions are removed. In this selection time interval 304, the filtered-noise field can be used that is disclosed in, for example, RAPID COMMUNICATIONS IN MASS SPECTROMETRY, VOL 7, 1086–1089 (1993). In the dissociation time interval, 305, the predetermined m/z ions selected in the selection time interval 304 are energized and forced to collide with helium gas within the mass spectrometer to produce fragment ions. In order to energize the ions, it is necessary that a high frequency voltage be applied between the end cap electrodes to accelerate the ions within the mass spectrometer. When the accelerated ions collide with the helium gas, part of the kinetic energy of the ions is converted to the internal energy of ions. During the time when the ions repeatedly collide with the helium gas, the internal energy is accumulated to break the weak chemical bonds of the ions, thus causing dissociation.

Since the tandem mass spectrometry has ion loss in the time intervals of selection and dissociation, it is necessary to trap sufficient amounts of ions in the ion trapping time interval 302 in order to acquire satisfactory mass spectra of fragment ions. Therefore, the ion trapping time interval 302, analyzing time interval 303, selection time interval 304, dissociation time interval 305 and residual ion removing time interval 301 are selected to be typically 0.40 second, 0.05 second, 0.03 second, 0.01 second and 0.01 second, respectively. Thus, the mass spectrum is acquired once in 0.5 second.

In the field of analysis, the mass spectrometry is used for various intended purposes. When the mass spectrometry is used for the detecting device, however, there are different points from the normal analysis.

While the normal analysis treats a very large number of ingredients, the detecting device detects extremely limited substances. Selecting and detecting a few main components can find a bomb, for example, which is produced by mixing various different detonating explosives. In addition, the normal analysis determines the value of the concentration of substance, while determination of only the presence or absence of the object suffices for the detecting.

Figure 7:
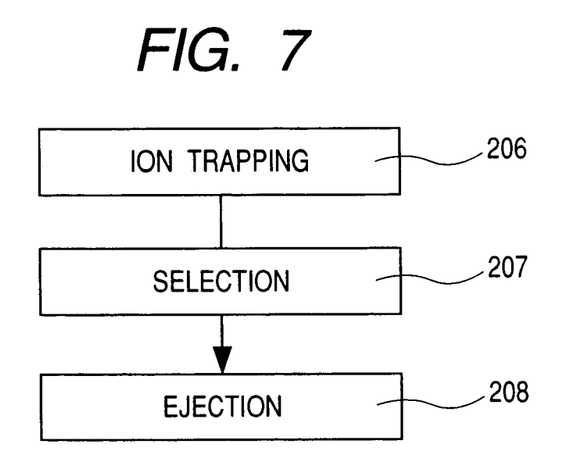
FIG. 7 is a diagram showing the procedure of spectrometry in the embodiment of the invention.
Figure 8:
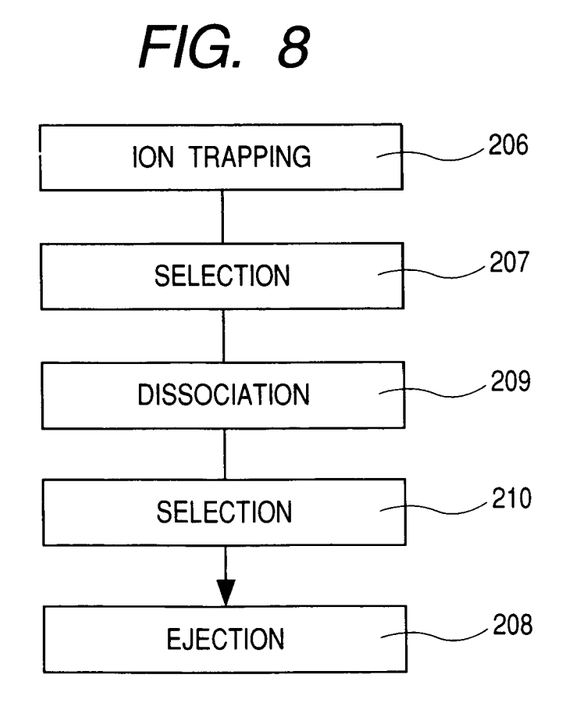
FIG. 8 is a flowchart of the tandem mass spectrometry.

Thus, the method of operating the mass spectrometer particularly effective in the detecting device will be described with reference to FIG. 6. When the trapped ions are ejected out of the ion trap mass spectrometer, the ejection efficiency varies depending on the mass scanning speed. In other words, in the analyzing time interval 303 of FIG. 5, when the rate of increase of the amplitude of the voltage applied to the ring electrode is increased so that the analyzing time interval 303 can be completed in a short time, the amount of ions ejected out of the spectrometer and arriving at the detector increases and thus the sensitivity is improved. However, when the rate of increase of the voltage amplitude applied to the ring electrode is raised in the analyzing time interval 303, the mass resolution is reduced, and it is not known exactly when the ions are ejected. Thus, the measured m/z values deviate from the correct values. For this reason, when the ion trap mass spectrometer is operated, a step 207 for selecting particular ions (corresponding to the selection time 307) is provided between a step 206 for ion trap (corresponding to the ion trapping time interval 302) and a step 208 for ejecting ions (corresponding to the analyzing time interval 303) as shown in FIG. 7. That is, limiting the m/z of ions remaining within the mass spectrometer compensates for the reduction of the resolution due to the fast mass scanning. Specifically, when amphetamine is detected, the m/z-136 positive ions are first checked. Thus, in step 206 the ions generated by the ion source are trapped within the mass spectrometer, and in step 207 the ions other than the m/z-136 ions are removed and the m/z-136 ions are selectively caused to remain. Then, in step 208 for ejecting ions, fast mass scanning is made so that the ions remaining within the mass spectrometer can be effectively ejected out of the mass spectrometer. Thus, since the m/z-136 ions definitely arrive at the detector, precise mass selection is not necessary in the step 208, so that the analyzing time can be reduced and that high-sensitive detecting can be performed. This method is effective not only for the screening time but also for the case of fully examining by tandem mass spectrometry. A step 210 for selecting the m/z of ions remaining within the mass spectrometer can be provided between a step 209 for dissociation and the step 208 for ejecting ions as shown in FIG. 8.

Figure 9:
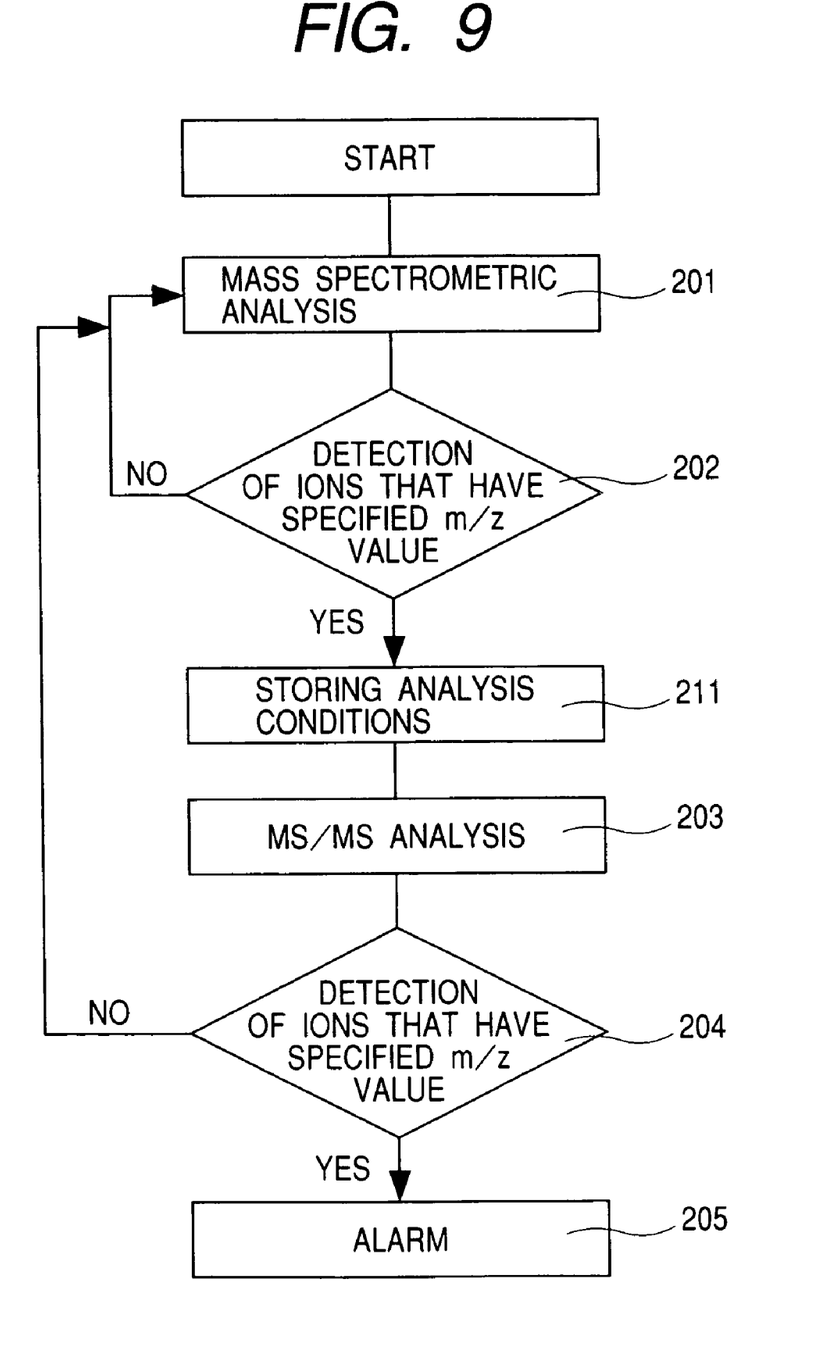
FIG. 9 is a diagram showing the algorithm of another embodiment of the invention.

Moreover, in this method, since the kind of object to be detected is limited, the database of objects is created on the data processor, and effectively used for the detecting. More specifically, in the tandem mass spectrometry, the optimum values of the length of the dissociation time and the amplitude of the high frequency voltage applied to the end cap electrodes to energize the ions at the time of dissociation are dependent upon the chemical substance to be detected. Therefore, a step 211, as shown in FIG. 9, is provided to examine the optimum analysis conditions for the components of each detected object to create a database, and when the operator feels the suspicion of the presence of a particular substance in the fast mode, to refer to the database at the time of shifting to the detailed checking mode so that the optimum analysis conditions for this substance can be read in. Thus, a satisfactory mass spectrum of fragment ions can be obtained, and precise decision can be made. For example, the optimum analysis conditions for each of various banned chemicals such as amphetamine and cocaine are examined to create a database, and the analysis conditions for amphetamine when amphetamine is suspected or for cocaine when cocaine is suspected are read out from the database and analyzed.

Figure 10:
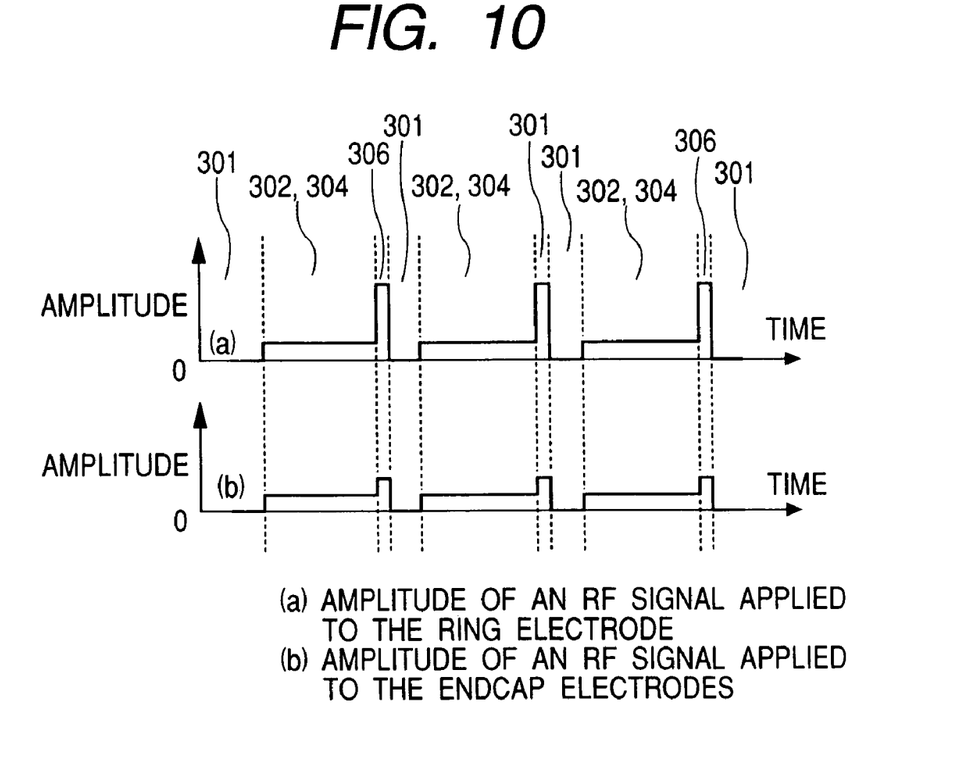
FIG. 10 is a timing chart of the high-frequency voltage applied to the ring electrode and end cap electrode.
Figure 11:
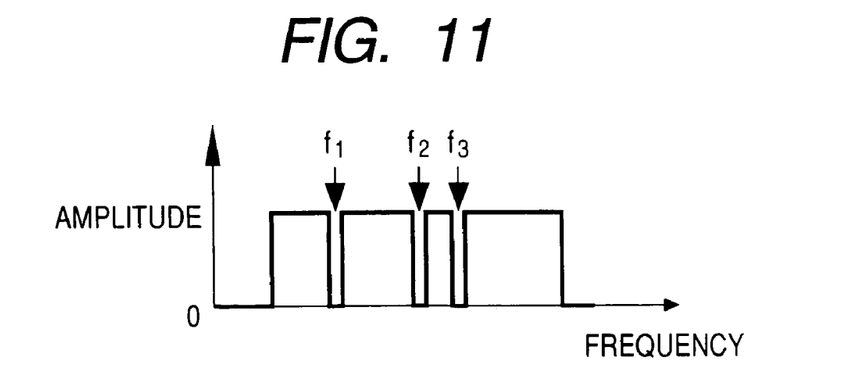
FIG. 11 is a diagram showing the frequency of the voltage applied to the end cap electrode during the trap and selection time interval.

While the substance to be detected is ionized and followed by the screening based on the m/z of ions in the above description, the screening can be performed without necessarily specifying the m/z of ions by mass isolation. FIGS. 10 and 11 are diagrams useful for explaining the second embodiment of the invention in which the screening is made according to the ion current value. FIG. 10 is a timing chart of high frequency voltage applied to the ring electrode and end cap electrodes. Although the ion trapping time interval 302 and ion selection time interval 304 may be sequentially provided as in FIG. 6, an ion trapping and selection time interval 302, 304 for simultaneously trapping and selecting ions is provided as in FIG. 10. FIG. 11 shows the frequency of the high frequency voltage applied to the end cap electrodes at the trapping/selection time interval 302, 304. The ions trapped within the ion trap mass spectrometer have easy-to-resonate frequencies according to the m/z. Thus, when a signal including frequency components other than those (f1, f2, f3) corresponding to the m/z of the ions of the substance to be detected is applied to the electrodes, only the ions having the target m/z are trapped at the trapping/selection time interval 302, 304. Then, an ion ejection time interval 306 is provided, and the ions remaining within the mass spectrometer are ejected in the ion ejection time interval, and detected by the detector. Here, when any signal is obtained, an alarm is issued or more detailed check mode is brought about. In this method, no time is taken for the mass spectrometry, and thus faster screening can be made.

Figure 12:
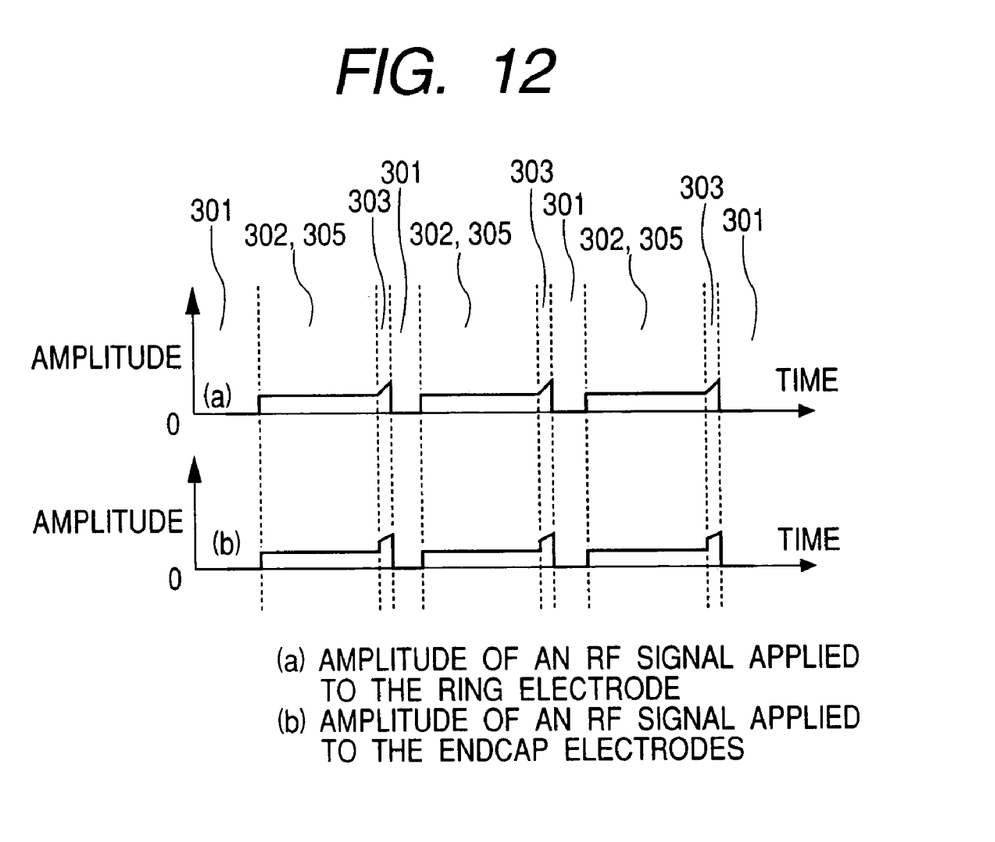
FIG. 12 is a diagram showing the situation in which the ion trap and dissociation are simultaneously progressed in the embodiment of the invention.
Figure 13:
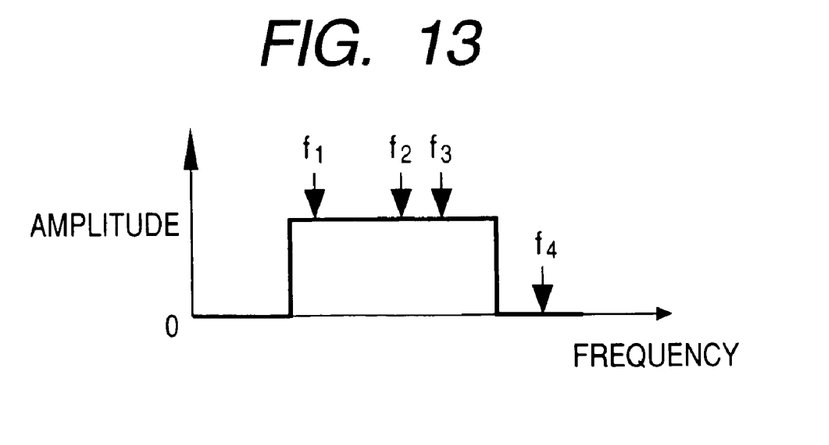
FIG. 13 is a diagram showing the frequency of the high-frequency voltage applied to the end cap electrode when the ion trap and dissociation are progressed at a time in the embodiment of the invention.

The third embodiment of the invention that is effective for detecting explosives will be described with reference to FIGS. 12 and 13. This embodiment is a screening method using ions derived from nitro groups obtained by dissociation of explosive. Energizing easily decomposes the nitro compound, and the nitro group tends to easily dissociate. Therefore, as shown in FIG. 12, a trap/dissociation time interval 302, 305 for simultaneously trapping and dissociating ions is provided. FIG. 13 shows the frequency of the high frequency voltage applied to the end cap electrodes in the trap/dissociation time interval 302, 305. A weak signal including the frequencies (f1, f2, f3) corresponding to the m/z of ions of a substance to be detected, but not including a frequency (f4) corresponding to the m/z of ions derived from the nitro group being detected is applied to the end cap electrodes. When the ions of an explosive being detected are trapped, they resonate with the high frequency voltage applied to the end cap electrodes, and as a result energized to collide with helium. At this time, the nitro group is dissociated, and thus the ions derived from the dissociated nitro group, for example, of $NO_2^-$ are detected in the analysis time interval 303, thus the screening being made. The merit of this method is that even if the sample also includes nitro compounds of other substance than that being detected, the dissociated nitro group is detected, and thus the object can be found.

Figure 14:
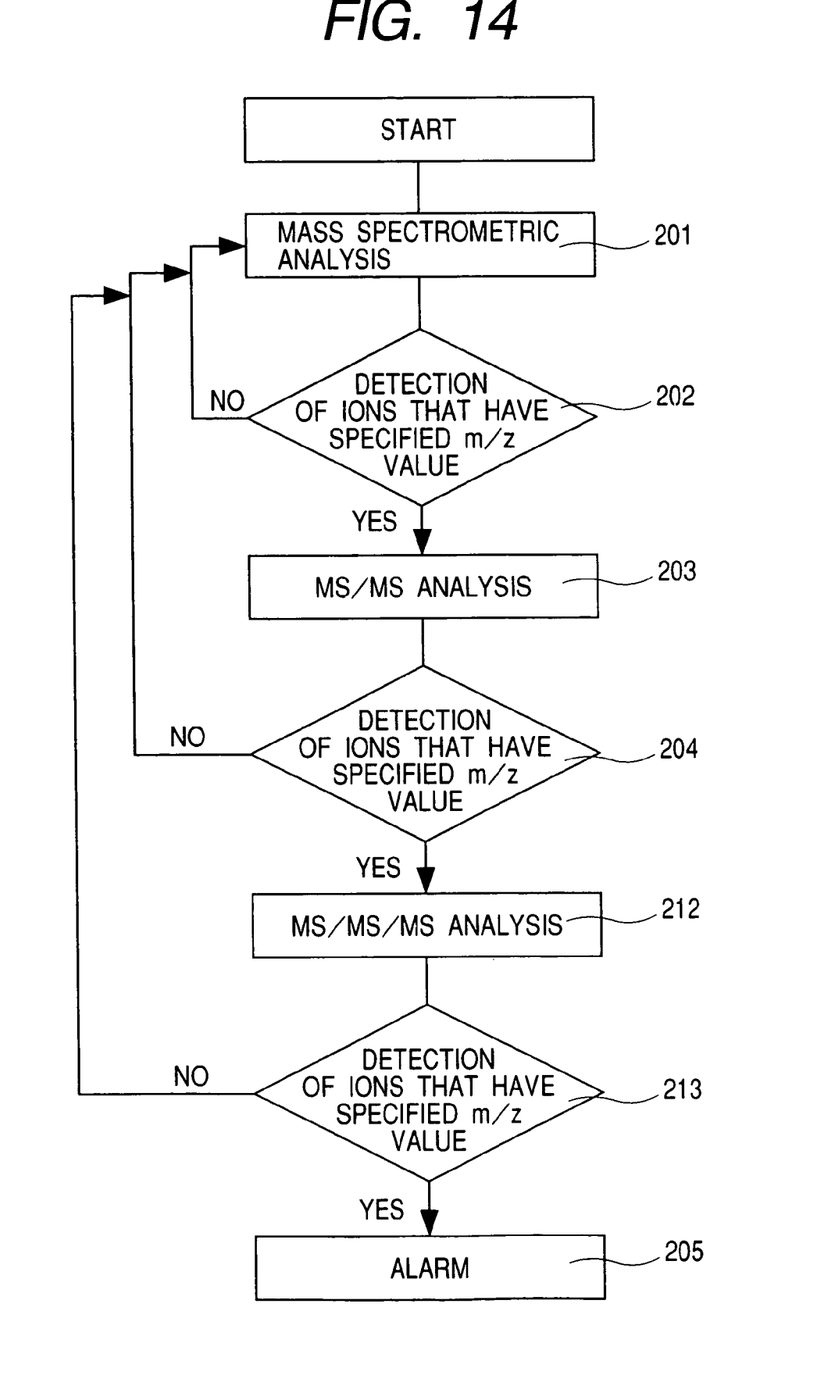
FIG. 14 is a diagram showing the algorithm of still another embodiment of the invention.

In the above method, higher-level mass spectrometry may be made in order to further increase the selectivity as shown in FIG. 14. In other words, a step 212 (called MS/MS/MS or $MS^3$) may be provided that selects ions of particular m/z from the fragment ions, dissociates them and makes mass spectrometry for the dissociated ions. These processes of selection, dissociation and mass spectrometry can be repeated until a satisfactory selectivity can be obtained (generally this is called $MS^n$).

Figure 15:
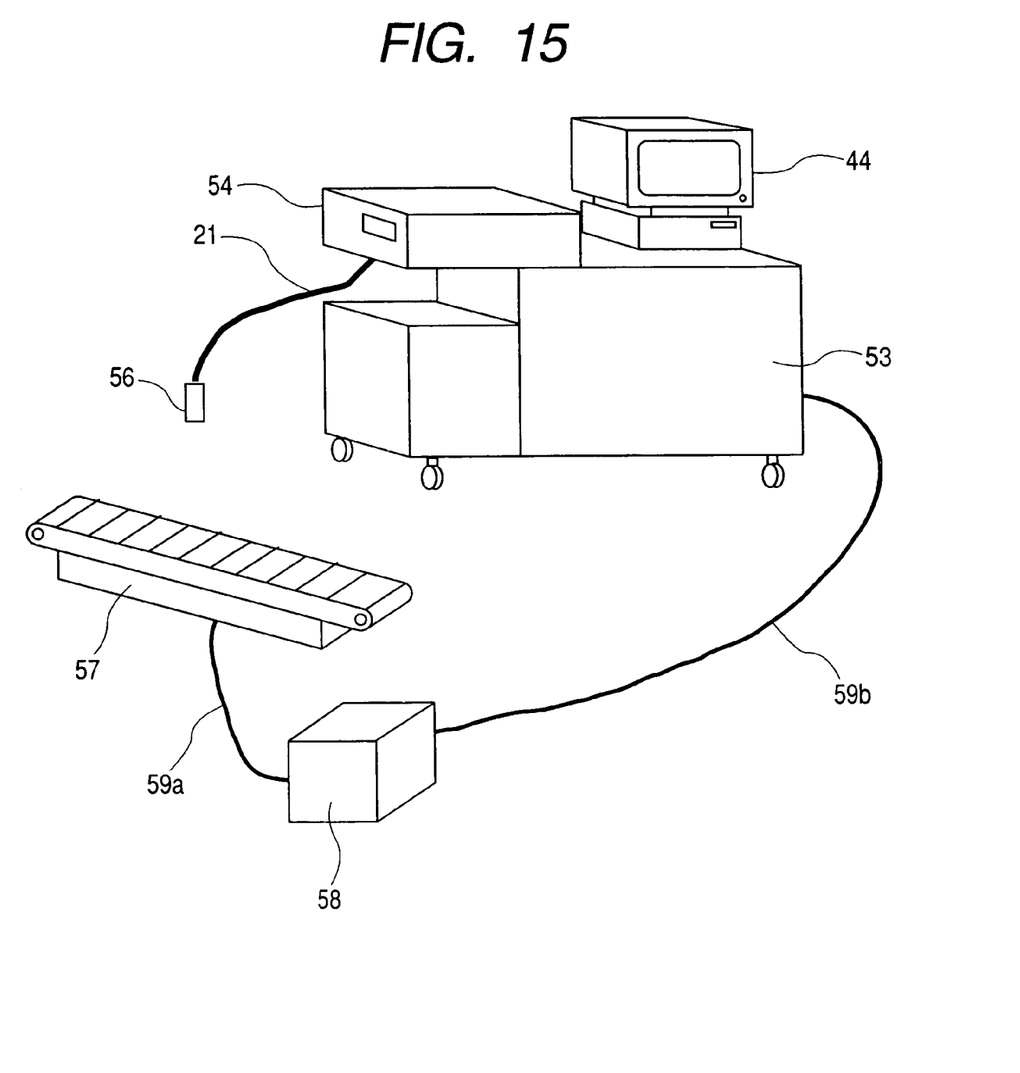
FIG. 15 is a diagram showing the construction of the device of the embodiment according to the invention.

In this invention, the time required for the detecting in the fast screening mode is different from that in the detailed check mode. Thus, as shown in FIG. 15, the detecting device according to the invention should be used together with a baggage carrying mechanism 57. The carrying mechanism 57, a carrying mechanism controller 58 and the detecting device body 53 are connected by signal lines 59a, 59b. In the screening mode, the carrying mechanism carries pieces of baggage at a constant speed, but when the main body 53 is switched to the detailed check mode in which the detecting is made in a few seconds, the speed of the carrying mechanism 57 is controlled to be slow.

Thus, according to the invention, the detecting can be made with high speed and with high selectivity, and thus the presence or absence of substances to be detected can be examined without disturbing the flow of baggage and passengers.

The invention claimed is:

1. An analyzing method using a tandem mass spectrometric apparatus, comprising:
    a first analysis step of acquiring a mass spectrum;
    a decision step of deciding if ions of a predetermined m/z value are present; and
    a second analysis step of acquiring a tandem mass spectrum according to the decision results from said first analysis step.

2. The analyzing method according to claim 1, further comprising a step of reading in analysis conditions from a database according to the decision results of said decision step.

3. The analyzing method according to claim 1, wherein said second analysis step has a trapping step of trapping said ions of said pre-determined m/z value, a selection step of selecting ions of said predetermined m/z value from said trapped ions, and an ejection step of ejecting said ions selected by said selection step.

4. An analyzing method using a tandem mass spectrometric apparatus, comprising:
    a first analysis step of acquiring a $MS^n$ mass spectrum;
    a decision step of deciding if ions of a predetermined m/z value are present; and
    a second analysis step of acquiring a $MS^{n-1}$ mass spectrum according to the decision results from said first analysis step.

5. A detecting method using a tandem mass spectrometric apparatus, comprising:
    a first step of acquiring a mass spectrum;
    a decision step of deciding if ions of a predetermined m/z are present; and
    a second step of acquiring a tandem mass spectrum according to decision results from said first step.

6. A detecting method using a tandem mass spectrometric apparatus, comprising:

a first step of acquiring a $MS^n$ mass spectrum;

a decision step of deciding if ions of a predetermined m/z value are present; and a second step of acquiring a $MS^{n-1}$ mass spectrum according to decision results from said first step.

7. A detecting method using a tandem mass spectrometric apparatus, comprising:

a first step of acquiring a mass spectrum;

a decision step of deciding if ions of a predetermined m/z are present;

a step of reading in analysis conditions from a database according to the decision results of said decision step; and a second step of acquiring a tandem mass spectrum.

8. A detecting method using a tandem mass spectrometric apparatus, comprising:

a first step of acquiring a $MS^n$ mass spectrum;

a decision step of deciding if ions of a predetermined m/value are present; and a step of reading in analysis conditions from a database according to the decision results of said decision step; and a second step of acquiring a $MS^{n+1}$ mass spectrum.

9. An analyzing method using a tandem mass spectrometric apparatus comprising:

a first step of acquiring a $MS^n$ mass spectrum;

a decision step of deciding if ions of a predetermined m/z value are present;

a step of reading in analysis conditions from a database according to decision results of said decision step; and a second step of acquiring a $MS^{n-1}$ mass spectrum.

* * * * *